United States Patent
Khosla et al.

(10) Patent No.: US 6,261,816 B1
(45) Date of Patent: *Jul. 17, 2001

(54) METHOD TO PRODUCE NOVEL POLYKETIDES

(75) Inventors: Chaitan Khosla, Stanford, CA (US); Rembert Pieper, Washington, DC (US); Guanglin Luo, Madison, CT (US); David E. Cane, Providence, RI (US); Camilla Kao, Palo Alto, CA (US)

(73) Assignees: Stanford University, Stanford, CA (US); Brown University Research Foundation, Providence, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/434,289

(22) Filed: Nov. 5, 1999

Related U.S. Application Data

(63) Continuation of application No. 08/896,323, filed on Jul. 17, 1997, now Pat. No. 6,066,721, which is a continuation-in-part of application No. 08/675,817, filed on Jul. 5, 1996, now Pat. No. 6,080,555.
(60) Provisional application No. 60/003,338, filed on Jul. 6, 1995.

(51) Int. Cl.[7] .................................................. C12N 9/00
(52) U.S. Cl. ...................... 435/183; 435/91.1; 435/91.4; 435/91.41; 435/91.42; 536/23.2
(58) Field of Search ................................ 435/252.2, 183, 435/91.1, 91.4, 91.41, 91.42; 536/23.2

(56) References Cited

U.S. PATENT DOCUMENTS 5,475,099  12/1995  Knauf et al. .
5,824,513  10/1998  Katz .

FOREIGN PATENT DOCUMENTS

WO 93/13663  7/1993  (WO) .
WO 95/08548  3/1995  (WO) .
WO 97/02358  1/1997  (WO) .
WO 97/13845  4/1997  (WO) .

OTHER PUBLICATIONS

Aparicio et al., "Limited Proteolysis and Active–Site Studies of the First Multienzyme Component of the Erythromycin-Producing Polyketide Synthase," J Biol Chem (1994) 269(11):8524–8528.

Bartel et al., "Biosynthesis of Anthraquinones by Interspecies Cloning of Actinorhodin Biosynthesis Genes in Streptomycetes: Clarification of Actinorhodin Gene Functions," J Bacteriol (1990) 172(9):4816–4826.

Beck et al., "The Multifunctional 6–Methylsalicylic Acid Synthase Gene of *Penicillium Patulum*. Its Gene Structure Relative to that of Other Polyketide Synthases," Eur J Biochem (1990) 192:487–498.

Bedford et al., "A Functional Chimeric Modular Polyketide Synthase Generated via Domain Replacement," Chemistry & Biology (1996) 3(10):827–831.

Bevitt et al., "6–Deoxyerythronolide–B Synthase 2 from *Saccharopolyspora erythraea*: Cloning of the Structural Gene, Sequence Analysis and Inferred Domain Structure of the Multifunctional Enzyme," Eur J Biochem (1992) 204:39–49.

Bibb et al., "Analysis of the Nucleotide Sequence of the *Streptomyces Glaucescens* tcml Genes Provides Key Information about the Enzymology of Polyketide Antibiotic Biosynthesis," Embo J (1989) 8(9):2727–2736.

(List continued on next page.)

*Primary Examiner*—Ponnathapu Achutamurthy
*Assistant Examiner*—Kathleen Kerr
(74) *Attorney, Agent, or Firm*—Morrison & Foerster LLP

(57) ABSTRACT

Modified PKS gene clusters which produce novel polyketides in an efficient system in a host cell or in a cell free extract are described.

10 Claims, 3 Drawing Sheets

OTHER PUBLICATIONS

Caballero et al., "Organisation and Functions of the actVA Region of the Actinorhodin Biosynthetic Gene Cluster of *Streptomyces coelicolor*," Mol Gen Genet (1991) 230:401–412.

Caffrey et al., "An Acyl–Carrier–Protein–Thioesterase Domain from the 6–Deoxyerythronolide B Synthase of *Saccharopolyspora erythraea*. High–Level Production, Purification and Characterisation in *Escherichia coli*," Eur J Biochem (1991) 195:823–830.

Caffrey et al., "Identification of DEBS 1, DEBS 2 and DEBS 3, the Multienzyme Polypeptides of the Erythromycin–Producing Polyketide Synthase from *Saccharopolyspora erythraea*," Febs Lett (1992) 304(2):225–228.

Cane et al., "Macrolide Biosynthesis. 7. Incorporation of Polyketide Chain Elongation Intermediates into Methymycin," J Am Chem Soc (1993) 115:522–526.

Corcoran et al., "The Biogenesis of Fatty Acids and Erythronolide–Like Substances in Mycelium–Free Extracts of *Streptomyces Erythreus*," in 5th International Congress of Chemotherapy, Vienna, Abstracts of Communications (1967) 35–40.

Corcoran, ed., in Antibiotics vol. IV Biosynthesis, Springer–Verlag, New York (1982) 145–150.

Cortes et al., "An Unusually Large Multifunctional Polypeptide in the Erythromycin–Producing Polyketide Synthase of *Saccharopolyspora erythraea*," Nature (1990) 348:176–178.

Daum et al., "Mutational Biosynthesis of New Antibiotics," Ann Rev Microbiol (1979) 33:241–265.

Davis et al., "Functional Mapping of a Polyketide Synthase from *aspergillus terreus* Involved in Lovastatin Synthesis," Abst. of the Genetics of Industrial Microorganisms Mtg. (1994) 288:192.

Dimroth et al., "Biosynthese Von 6–Methylsalicylsaure," Eur J Biochem (1970) 13:98–110.

Donadio et al., "Modular Organization of Genes Required for Complex Polyketide Biosynthesis," Science (1991) 252:675–679.

Donadio et al., "Organization of the Enzymatic Domains in the Multifunctional Polyketide Synthase Involved in Erythromycin Formation in *Saccharopolyspora erythraea*," Gene (1992) 111:51–60.

Donadio et al., "Biosynthesis of the Erythromycin Macrolactone and a Rational Approach for Producing Hybrid Macrolides," Gene (1992) 115:97–103.

Donadio et al., "An Erythromycin Analog Produced by Reprogramming of Poyketide Synthesis," Proc Natl Acad Sci USA (1993) 90:7119–7123.

Dutton et al., "Avermectin Biosynthesis. Intact Incorporation of a Diketide Chain–Assembly Intermediate into the Polyketide Macrocycle Ring," Tetrahedron Letters (1994) 35(2):327–330.

Dutton et al., "Novel Avermectins Produced by Mutational Biosynthesis," J Antibiot (1991) 44(3):357–365.

Fernandez–Moreno et al., "The act Cluster Contains Regulatory and Antibiotic Export Genes, Direct Targets for Translational Control by the bldA tRNA Gene of Streptomyces," Cell (1991) 66:769–780.

Fernandez–Moreno et al., "Nucleotide Sequence and Deduced Functions of a Set of Cotranscribed Genes of *Streptomyces coelicolor* A3(2) Including the Polyketide Synthase for the Antibiotic Actinorhodin," J Biol Chem (1992) 267:19278–19290.

Gokhale et al., "Functional Orientation of the Acyltransferase Domain in a Module of the Erythromycin Polyketide Synthase," Biochemistry (1998) 37:2524–2528.

Hallam et al., "Nucleotide Sequence, Transcription and Deduced Function of a Gene Involved in Polyketide Antibiotic Synthesis in *Streptomyces coelicolor*," Gene (1988) 74:305–320.

Hopwood et al., "Product of 'Hybrid' Antibiotics by Genetic Engineering," Nature (1985) 314(6012):642–644.

Hopwood et al., "Genes for Polyketide Secondary Metabolic Pathways in Microorganisms and Plants," Secondary Metabolites: Their Function and Evolution, Wiley Chichester (Ciba Foundation Symposium 171) (1992) 88–112.

Hunaiti et al., "Source of Methylmalonyl–Coenzyme A for Erythromycin Synthesis: Methylmalonyl–Coenzyme A Mutase from *Streptomyces erythreus*," Antimicrobial Agents and Chemotherapy (1984) 25(2):173–178.

Kao et al., "Gain of Function Mutagenesis of the Erythromycin Polyketide Synthase. 2. Engineered Biosynthesis of an Eight–Membered Ring Tetraketide Lactone," J Am Chem Soc (1997) 119(46):11339–11340.

Kao et al., "Manipulation of Macrolide Ring Size by Directed Mutagenesis of a Modular Polyketide Synthase," J Am Chem Soc (1995) 117(35):9105–9106.

Kao et al., "Evidence for Two Catalytically Independent Clustersof Action Sites in a Functional Modular Polyketide Synthase," Biochemistry (1996) 35(38):12363–12368.

Kao et al., "Engineered Biosynthesis of Structurally Diverse Tetraketides by a Trimodular Polyketide Synthase," J Am Chem Soc (1996) 118(38):9184–9185.

Kao et al., "Engineered Biosynthesis of a Complete Macrolactone in a Heterologous Host," Science (1994) 265:509–512.

Khosla et al., "Genetic Construction and Functional Analysis of Hybrid Polyketide Synthases Containing Heterologous Acyl Carrier Proteins," J Bacteriol (1993) 175(8):2197–2204.

Kramer et al., "Rational Design and Engineered Biosynthesis of a Novel 18–Carbon Aromatic Polyketide," J Am Chem Soc (1997) 119(4):635–639.

Kuhstoss et al., "Production of a Novel Polyketide Through the Construction of a Hybrid Polyketide Synthase," Gene (1996) 183:231–236.

Lanz et al., "The Role of Cysteines in Polyketide Synthase," J Biol Chem (1991) 266(15):9971–9976.

Leadlay et al., "The Erythromycin–Producing Polyketide Synthase," Biochem Soc Transactions (1993) 21:218–222.

MacNeil et al., "Complex Organization of the *Streptomyces avermitilis* Genes Encoding the Avermectin Polyketide Synthase," Gene (1992) 115:119–125.

Malpartida et al., "Molecular Cloning of the Whole Biosynthetic Pathway of a Streptomyces Antibiotic and its Expression in a Heterologous Host," Nature (1984) 309:462–464.

Malpartida et al., "Physical and Genetic Characterisation of the Gene Cluster for the Antobiotic Actinorhodin in *Streptomyces coelicolor* A3(2)," Mol Gen Genet (1986) 205:66–73.

Marsden et al., "Sterespecific Acyl Transfers on the Erythromycin–Producing Polyketide Synthase," Science (1994) 263:378–380.

McDaniel et al., "Gain–of–Function Mutagenesis of a Modular Polyketide Synthase," J Am Chem Soc (1997) 119(18):4309–4310.

Oliynyk et al., "A Hybrid Modular Polyketide Synthase Obtained by Domain Swapping," Chem Biol (1996) 3(10):833–839.

Omura et al., "Inhibition of the Biosynthesis of Leucomycin, A Macrolide Antibiotic, by Cerulenin," J Biochem (1974) 75:193–195.

Pereda et al., "The Loading Domain of the Erythromycin Polyketide Synthase is not Essential for Erythromycin Biosynthesis in *Saccharopolyspora erythraea*," Microbiology (1998) 144:543–553.

Pieper et al., "Remarkably Broad Substrate Specificity of a Modular Polyketide Synthase in a Cell–Free System," J Am Chem Soc (1995) 117(45):11373–11374.

Pieper et al., "Cell–Free Synthesis of Polyketides by Recombinant Erythromycin Polyketide Synthesis," Nature (1995) 378:263–266.

Pieper et al., "Purification and Characterization of Bimodular and Trimodular Derivatives of the Erythromycin Polyketide Synthase," Biochemistry (1997) 36(7):1846–1851.

Pieper et al., "Erythromycin Biosynthesis: Kinetic Studies on a Fully Active Modular Polyketide Synthase Using Natural and Unnatural Substrates," Biochemistry (1996) 35:2054–2060.

Roberts et al., "[$^3$H]Tetrahydrocerulenin, a Specific Reagent for Radio–Labelling Fatty Acid Synthases and Related Enzymes," Febs Lett (1983) 159(1,2):13–16.

Roberts et al., "Use of [$^3$H]Tetrahydrocerulenin to Assay Condensing Enzyme Activity in *Streptomyces erythreus*," Biochem Soc Transactions (1984) 12:642–643.

Rudd et al., "Genetics of Actinorhodin Biosynthesis by *Streptomyces Coelicolor* A3(2)," J Gen Microbiol (1979) 114:35–43.

Shen et al., "Enzymatic Synthesis of a Bacterial Polyketide from Acetyl and Malonyl Coenzyme A," Science (1993) 262:1535–1540.

Sherman et al., "Structure and Deduced Function of the Granaticin–Producing Polyketide Synthase Gene Cluster of *Streptomyces violaceoruber* Tü22," Embo J (1989) 8(9):2717–2725.

Sherman et al., "Functional Replacement of Genes for Individual Polyketide Synthase Components in *Streptomyces coelicolor* A3(2) by Hetergeneous Genes from a Different Polyketide Pathway," J Bacteriol (1992) 174(19):6184–6190.

Spencer et al., "Purification and Properties of 6–Methylsalicylic Acid Synthase from *Penicillium patulum*," Biochem J (1992) 288:839–846.

Wawszkiewicz et al., "Propionyl–CoA Dependent $H^{14}CO_3$–Exchange into Methymalonyl–CoA in Extracts of *Streptommyces erythraeus*," Biochemische Zietschrift (1964) 340:213–227.

Wiesmann et al., "Polyketide Synthesis In Vitro on a Modular Polyketide Synthase," Chem Biol (1995) 2(9):583–589.

Kim et al. Heterologous Expression of an Engineered Biosynthetic Pathway: Functional Dissection of Type II Polyketide Synthase Components in Streptomyces Species. J. of Bacteriology (1995) 177(5):1202–1207, Mar. 1995.*

* cited by examiner

1: R=Methyl
6: R=n-Propyl
7: R=Phenyl

9: R=Methyl
10: R=n-Propyl
11: R=Phenyl

METHOD TO PRODUCE NOVEL POLYKETIDES

CROSS REFERENCE TO RELATED APPLICATIONS

This application is a continuation of U.S. Ser. No. 08/896,223 filed Jul. 17, 1997 now U.S. Pat. No. 6,066,721 which is a continuation-in-part of U.S. Ser. No. 08/675,817, filed Jul. 5, 1996 now U.S. Pat. No. 6,080,555 which claims priority under 35 USC 119(e)(1) from provisional application serial No. 60/003,338 filed Jul. 6, 1995. The contents of these applications are incorporated herein by reference.

STATEMENT OF RIGHTS TO INVENTIONS MADE UNDER FEDERALLY SPONSORED RESEARCH

This invention was made with U.S. government support from the National Institutes of Health (GM22172 and CA66736-01). The government has certain rights in this invention.

TECHNICAL FIELD

The invention relates to methods to synthesize polyketides which are novel using modified modular polyketides syntheses (PKS) which cannot utilize a natural first module starter unit.

1. Background Art

Modular polyketide syntheses are typified by the organization of deoxyerythronolide B synthase (DEBS) which produces β-deoxyerythronolide B (6-dEB) the parent macrolactone of the broad spectrum antibiotic erythromycin. DEBS consists of three large polypeptides each containing about 10 distinctive active sites. FIG. 1 shows, diagramatically, the nature of the three DEBS modules encoded by the three genes eryAI, eryAII and eryAIII.

Various strategies have been suggested for genetic manipulation of PKS to produce novel polyketides. New polyketides have been generated through module deletion (Kao, C. M. et al., . *J. Am. Chem. Soc.* (1995) 117:9105–9106; Kao, C. M. et al, *J. Am. Chem. Soc.* (1996) 118:9184–9185). Also reported to provide novel polyketides are loss of function mutagenesis within reductive domains (Donadio, S. et al., *Science* (1991) 252:675–679; Donadio, S. et al, *Proc. Natl. Acad. Sci. USA* (1993) 90:7119–7123; Bedford, D. et al., *Chem. Biol.* (1996) 3:827–831) and replacement of acyl transferase domains to alter starter or extender unit specificity (Oliynyk, M et al., *Chem. Biol.* (1996) 3:833–839; Kuhstoss, S. et al., *Gene* (1996) 183:231–236), as well as gain of function mutagenesis to introduce new catalytic activities within existing modules McDaniel, R. et al., *J. Am. Chem. Soc.* (1997) in press). In some of these reports, downstream enzymes in the polyketide pathway have been shown to process non-natural intermediates. However, these methods for providing novel polyketides suffer from the disadvantages of requiring investment in cloning and DNA sequencing, the systems used being limited to producer organisms for which gene replacement techniques have been developed, primer and extender units that can only be derived from metabolically accessible CoA thioesters, and the fact that only limited auxiliary catalytic functions can be employed.

The DEBS system in particular has been shown to accept non-natural primer units such as acetyl and butyryl-CoA (Wiesmann, K E H et al, *Chem. Biol.* (1995) 2:583–589; Pieper, R. et al, *J. Am. Chem. Soc.* (1995) 117:11373–11374) as well as N-acetylcysteamine (NAC) thioesters of their corresponding ketides (Pieper, R. et al., *Nature* (1995) 378:263–266). However, it has become clear that even though such unnatural substrates can be utilized, competition from the natural starter unit has drastically lowered yield. Even if starter units are not supplied artificially, they can be inherently generated from decarboxylation of the methlmalonyl extender units employed by the DEBS system (Pieper, R. et al., *Biochemistry* (1996) 35:2054–2060; Pieper, R. et al., *Biochemistry* (1997) 36:1846–1851).

Accordingly, it would be advantageous to provide a mutant form of the modular polyketide synthesis system which cannot employ the natural starter unit. Such systems can be induced to make novel polyketides by supplying, instead, a suitable diketide as an NAC thioester or other suitable thioester. Mutations have been made in the past to eliminate the competition from natural materials (Daum, S. J. et al., *Ann. Rev. Microbiol.* (1979) 33:241–265). Novel avermectin derivatives have been synthesized using a randomly generated mutant strain of the avermectin producing organism (Dutton, C. J. et al., *Tetrahedron Letters* (1994) 35:327–330; Dutton, C. J. et al., *J. Antibiot.* (1991) 44:357–365). This strategy is, however, not generally applicable due to inefficiencies in both mutagenesis and incorporation of the substrates.

Thus, there is a need for a more efficient system to prepare novel polyketides by inhibiting competitive production of the natural product.

2. Disclosure of the Invention

The invention is directed to methods to prepare novel polyketides using modified modular polyketide synthase systems wherein directed modification incapacitates the system from using its natural starting material. Novel polyketides can then be synthesized by overriding the starter module and supplying a variety of suitable diketide substrates.

Thus, in one aspect, the invention is directed to a method to prepare a novel polyketide which method comprises providing a thioester diketide substrate to a modular PKS comprising at least two modules under conditions wherein said substrate is converted by said modular PKS to a product polyketide, wherein said PKS has been modified to prevent its utilization of the native starter unit. In other aspects, the invention is directed to the modified modular PKS which is disarmed with respect to utilization of the native starter substrate supplying the initial two carbon unit, and to suitable cells modified to contain this disarmed PKS. The invention is further directed to recombinant materials for production of the modified PKS and to the novel polyketides produced by this system.

MODES OF CARRYING OUT THE INVENTION

Figure 1:
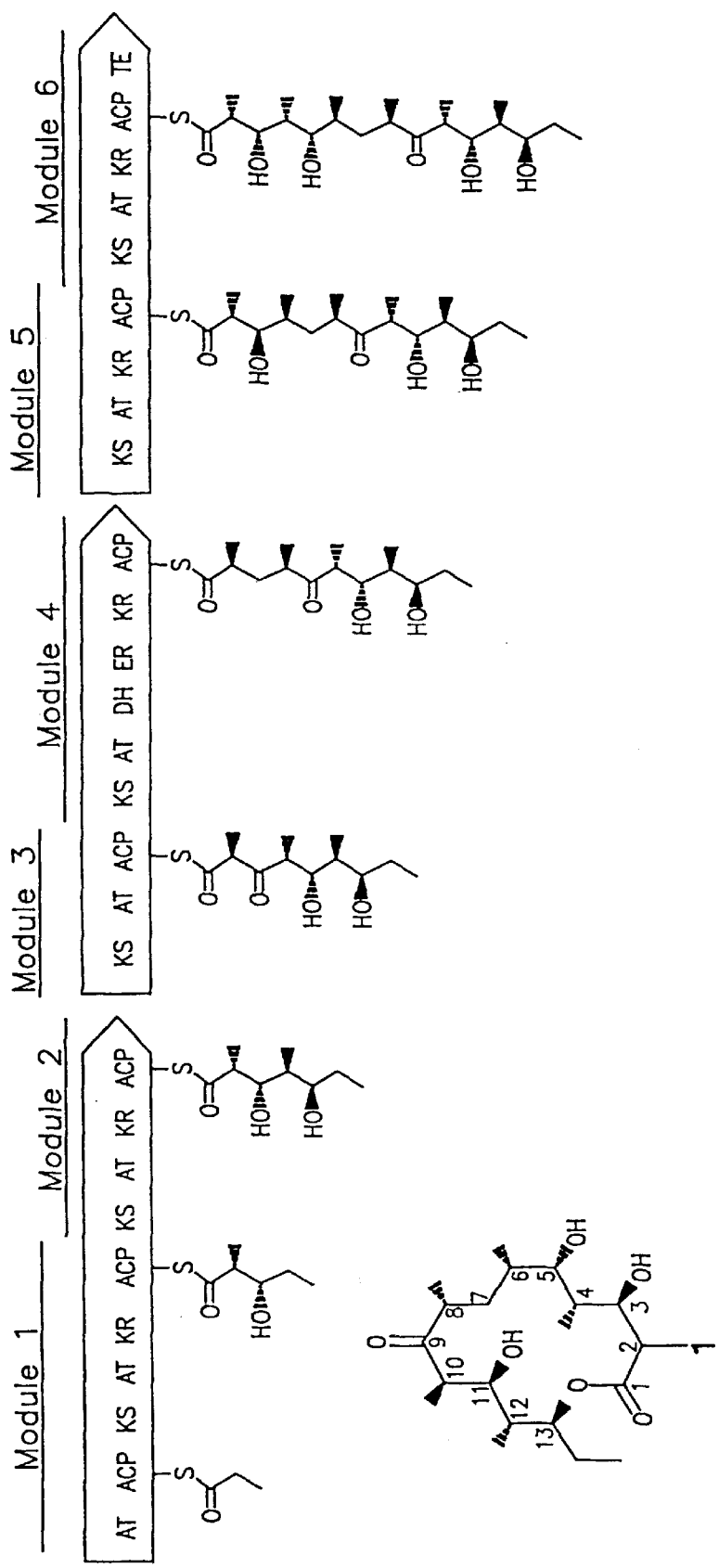
FIG. 1 shows a schematic representation of the DEBS modular PKS

The invention provides modular PKS systems which are disarmed with respect to loading the native starting material and their corresponding genes. In a particularly preferred embodiment, the ketosynthase (KS) of module 1 is inactivated so as to prevent competition from the native starter unit. Other approaches to similarly disarming the PKS involve inactivating the acyl transferase (AT) or acyl carrier protein (ACP) functions of module 1.

The PKS of the invention must contain at least two modules but may contain additional modules and, indeed be complete synthase systems. While the DEBS PKS system is used to illustrate the invention, any modular PKS can be used, such as the modular PKS resulting in the production of avermectin, rapamycin and the like. Suitable mutations can be introduced by known site specific mutagenesis techniques.

Other micro-organisms such as yeast and bacteria may also be used. The novel polyketides may be synthesized in a suitable hosts, such as a Streptomyces host, especially a Streptomyces host modified so as to delete its own PKS. The polyketides may also be synthesized using a cell-free system by producing the relevant PKS proteins recombinantly and effecting their secretion or lysing the cells containing them. A typical cell-free system would include the appropriate PKS, NADPE and an appropriate buffer and substrates required for the catalytic synthesis of polyketides. To produce the novel polyketides thioesters of the extender units are employed along with the thioester of a diketide.

The following examples are intended to illustrate but not to limit the invention.

PREPARATION A

Starting Materials

Streptomyces coelicolor CH999, which has been engineered to remove the native PKS gene cluster is constructed as described in PCT publication WO 95/08548. pRM5, a shuttle plasmid used for expressing PKS genes in CH999 was also described in that application. Plasmid pCK7 which contains the entire DEBS modular system was described in the foregoing PCT publication as well.

EXAMPLE 1

Preparation of DEBS 1+2+TE

A modified DEBS PKS system containing only modules 1 and 2 and thioesterase (TE) activity, designated DEBS 1+2+TE, was subjected to site directed mutagenesis to inactivate module 1 KS by replacing the active site cysteine residue in the signature sequence by alanine. The signature sequnece consists of 3 serine residues bracketed at the N-terminus by cysteine and at the C-terminus by leucine The resulting expression plasmid, designated pKAO179, encodes a 2-module PKS which is inactive under the standard reaction conditions for synthesis of the native product, i.e., propionyl-CoA, methylmalonyl-CoA, and NADPH. The details of this construction are set forth in Kao, C. M. et al, Biochemistry (1996) 35:12363–12368. When provided with the diketide thioester (2S, 3R)-2-methyl-3,3-hydroxy-pentanoyl-N-acetylcysteamine thioester, and with methylmalonyl-CoA, and NADPH, the triketide product is obtained.

The triketide product is produced under these conditions when the PKS is incubated in a cell-free system or can be duplicated in vivo by providing the appropriate diketide thioester analogs to actively growing cultures of CH999 containing the modified expression plasmid:

A culture of S. coelicolor CH999/pKAO179 is established by inoculation of 200 mL of SMM medium (5% PEG-800, 0.06% $MgSO_4$, 0.2% $(NH_4)_2SO_4$, 25 mM TES, pH 7.02, 25 mM $KH_2PO_4$, 1.6% glucose, 0.5% casaimino acids, trace elements) with spores. The culture is incubated at 30° C. with shaking at 325 rpm. A solution of (2S, 3R)-2-methyl-3-hydroxypentanoyl N-acetlycysteamine thioester (100 mg) and 4-pentynoic (15 mg) in 1 mL of methylsulfoxide is added to the culture in three parts; after 50 hours (400 µL); after 62 hours (300 µL); and after 86 hours (300 µL). After a total of 144 hours, the culture is centrifuged to remove mycelia. The fermentation broth is saturated with NaCl and extracted with ethyl acetate (5×100 µL). The combined organic extract is dried over $Na_2SO_4$, filtered, and concentrated. Silica gel chromatography yields (2R, 3S, 4S, 5R)-2,4-dimethyl-3,5-dihydroxy-n-heptanoic acid δ-lactone.

EXAMPLE 2

Preparation of Polyketides from the DEBS Cluster

The active site mutated module 1 KS domain of the eryAI (DEBS 1 gene) is provided on aderivative of plasmid pCK7, (Kao, C. M., et al., *Sceince* (1994) 265:509–512; which contains the eryAI, eryAII (DEBS 2) and eryAIII (DEBS 3 genes) under control of the acti promoter. Expression from this plasmid renamed pJRJ2 results in a suitably modified fuill length PKS system. pJRJ2 was transformed into CH999 and transformats grown on R2YE medium. No detectable 6 DEB-like products were produced.

In more detail, lawns of CH999/pJRJ2 were grown at 30° C. on R2YE agar plates containing 0.3 mg/ml sodium propionate. After three days, each agar plate was overlayed with 1.5 mL of a 20 mM substrate solution in 9:1 water-:DMSO. After an additional 4 days, the agar media (300 mL) were homogenized and extracted three times with ethyl acetate. The solvent was dried over magnesium sulfate and concentrated. Concentrated extracts were purified by silica gel chromatography (gradient of ethyl acetate in hexanes) to afford products.

However, when compound 2, prepared by the method of Cane et al., *J. Am. Chem. Soc.* (1993) 115:522–526; Cane, D. E. et al., *J Antibiot.* (1995) 48:647–651, shown in FIG. 2 (the NAC thioester of the native diketide) was added to the system, the normal product, 6 dEB was produced in large quantities. Administration of 100 mg compound 2 to small scale cultures (300 ml grown on petri plates as described above), resulted in production of 30 mg 6 dEB, 18% yield.

EXAMPLE 3

Production of Novel Polyketides

Figure 2:
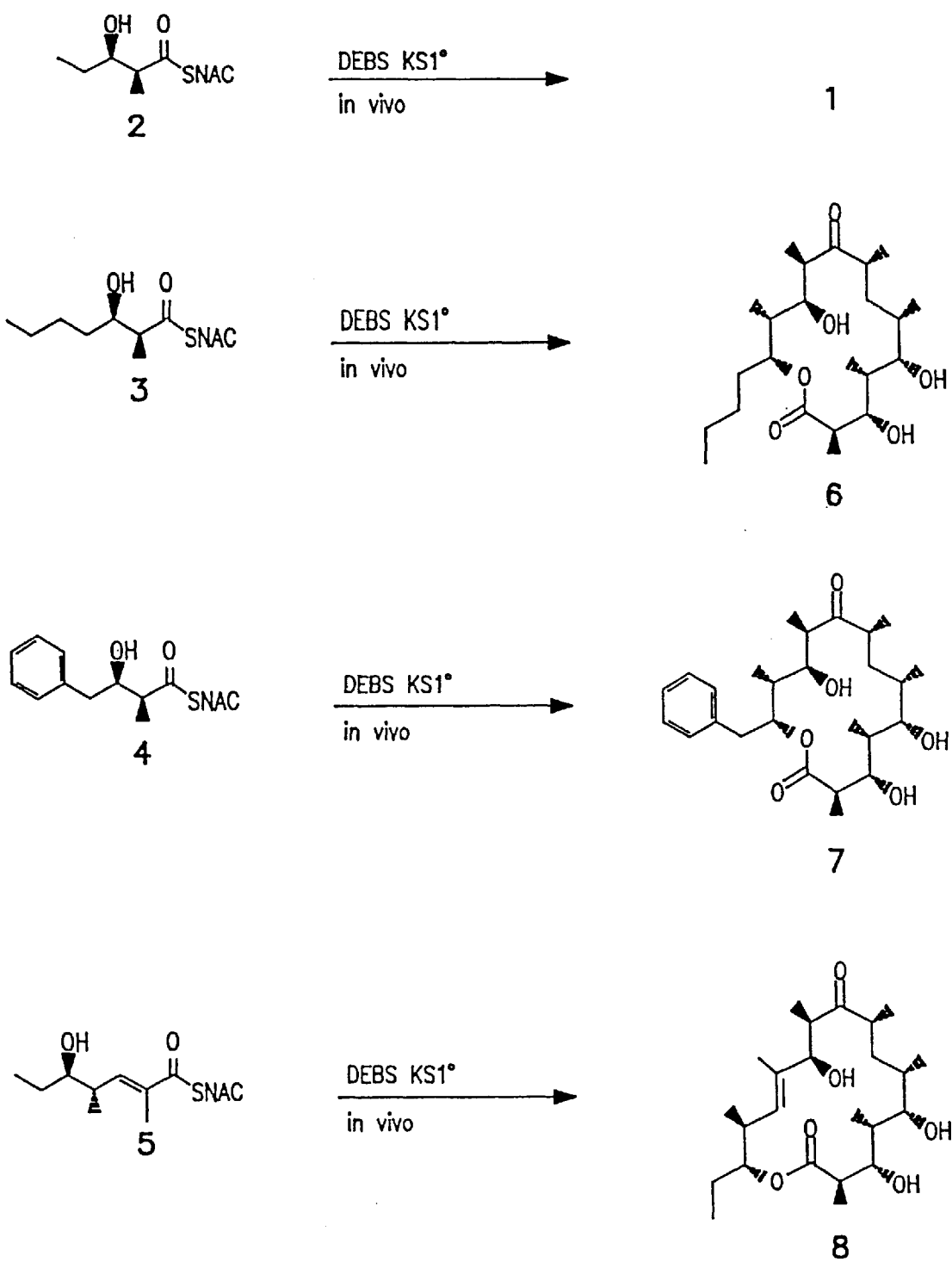
FIG. 2 shows the products of a modified DEBS construct wherein the ketosynthase in module 1 is disarmed.

Diketides with the structures shown in FIG. 2 as formulas 3, 4, and 5 were then administered to growing cultures of CH999/pJRJ2 under the conditions of Example 2. Compounds 3 and 4 were prepared as described for Substrate 2 but substituting valeraldehyde and phenylacetaldehyde, respectively for propionaldehyde in the aldol reactions. The preparation of Compound 5 was described by Yue, S. et al., *J. Am. Chem. Soc.* (1987) 109:1253–1255. Compounds 3 and 4 provided 55 mg/L of product 6 and 22 mg/L of product 7, respectively. Compound 5 resulted in the production of 25 mg/L of the 16 member lactone 8, an unexpected product.

EXAMPLE 4

Processing of the Polyketide Products

Figure 3:
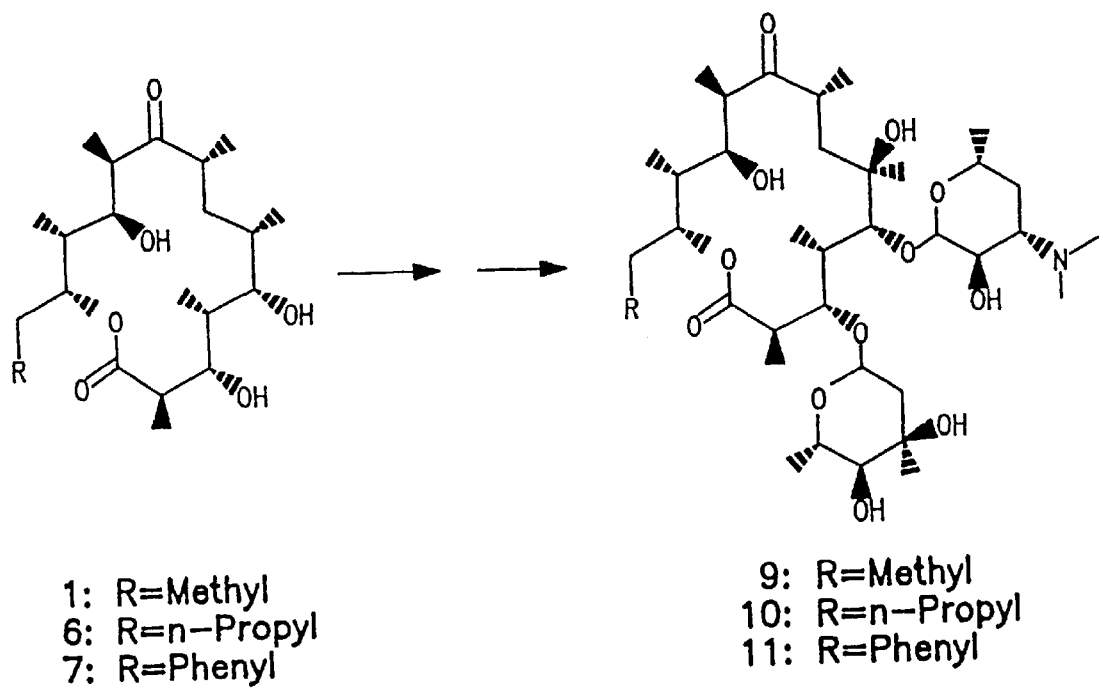
FIG. 3 shows the processing of 6-dEB derivatives to erythromycin-D derivatives.

The successful processing of unnatural intermediates by the "downstream" modules of DEBS prompted an experiment to determine whether the post-PKS enzymes in the erthromycin biosynthetic pathway might also accept unnatural substrates. In the natural producer organism, *Saccharopolyspora erythraea*, 6dEB undergoes several enzyme-catalyzed transformations. Oxidation at C6 and glycosylations at C3 and C5 afford erythromycin D (formula 9 in FIG. 3) and subsequent transformations afford erythromycins A, B, and C. *S. erythraea* mutant (A34) (Weber, J. M. et al., *J. Bactiol.* (1985) 164:425–433) is unable to synthesize 6dEB. This strain produces no erythromycin when grown on R2YE plates (as judged by the ability of extracts to inhibit growth of the erythromycin-sensitive bacterium *Bacillus cereus*). However, when 6dEB (which has no antibacterial activity) is added to the culture medium, extracts exhibited potent antibacterial activity.

Samples of 6dEB derivatives 6 and 7 were assayed for conversion by this strain. Partially purified extracts demonstrated inhibition of *B. cereus* growth, and mass spectrometry was used to identify the major components of the extracts as formula 10 in FIG. 3 (from 6) and formula 11 (from 7).

In more detail, purified 6 and 7 (5 mg dissolved in 7.5 mL 50% aqueous ethanol) were layered onto R2YE plates (200 mL media/experiment) and allowed to dry. *S. erythraea* A34 was then applied so as to give lawns. After 7 days of growth, the media were homogenized and extracted three times with 98.5:1.5 ethyl acetate:triethylamine. Pooled extracts from each experiment were dried over magensium sulfate and concentrated. Extracts were partially purified by silica gel chromatography (gradient of methanol and triethylamine in chloroform). The partially purified extracts were examined by TLC and mass spectrometry. For antibacterial activity analysis, filter discs were soaked in 400 $\mu$M ethanolic solutions of erythromycin D, 10 and 11, as well as a concentrated extract from *S. erythrea* A34 which had been grown without addition of any 6-dEB analogs. Disks were dried and laid over freshly-plated lawns of *Bacillus cereus*. After incubation for 12 h at 37° C., inhibition of bacterial growth was evident for all compounds but not for the control extract.

What is claimed is:

1. A method to produce a modified modular polyketide synthase (PKS) which modified PKS is incapable of incorporating a native starter unit substrate for said modular PKS but is able to incorporate a diketide substrate into at least a triketide said method comprising culturing recombinant host cells under conditions wherein an encoding nucleotide sequence is expressed to produce said modified modular PKS; and optionally recovering said modified modular PKS;

wherein said recombinant host cells contain a nucleic acid molecule, said nucleic acid molecule comprising a nucleotide sequence encoding at least a first and second module of said PKS, wherein said first module is immediately N-terminal to said second module and wherein said nucleotide sequence compnses a mutation such that the catalytic domain of the functional ketosynthase region of the first module of said encoded PKS is inactivated, said encoding nucleotide sequence operably linked to control sequences for its expression.

2. The method of claim 1 wherein said encoding nucleotide sequence is heterologous to said control sequences and/or to said host cell.

3. The method of claim 1 wherein the host cells are Streptomyces.

4. The method of claim 3 wherein the host cells are *S. coelicolor* CH999.

5. The method of claim 1 wherein said encoding nucleotide sequence encodes modules of 6-deoxyerythronolide B (6-dEB) synthase.

6. The method of claim 5 wherein said encoding nucleotide sequence encodes a complete 6-dEB synthase.

7. The method of claim 1 wherein said mutation alters only one amino acid in the catalytic domain of said ketosynthase region of said first module.

8. The method of claim 7 wherein said amino acid is cysteine.

9. The method of claim 8 wherein said cysteine is replaced by alanine.

10. A method to prepare a modified nucleic acid molecule, said nucleic acid molecule comprising a nucleotide sequence encoding at least a first and second module of a modular PKS, wherein said first module is immediately N-terminal to said second module and wherein said nucleotide sequence comprises a mutation such that the catalytic domain of the ketosynthase region of the first module of said encoded PKS is inactivated, said encoding nucleotide sequence operably linked to control sequences for its expression, which method comprises effecting said mutation in said nucleic acid molecule.

\* \* \* \* \*